United States Patent
Samain et al.

(10) Patent No.: US 12,201,207 B2
(45) Date of Patent: Jan. 21, 2025

(54) HAIR TREATMENT METHOD

(71) Applicant: L'OREAL, Paris (FR)

(72) Inventors: Henri Samain, Chevilly LaRue (FR); Jean-Luc Robinault, Saint-Ouen (FR)

(73) Assignee: L'OREAL, Paris (FR)

( * ) Notice: Subject to any disclaimer, the term of this patent is extended or adjusted under 35 U.S.C. 154(b) by 724 days.

(21) Appl. No.: 17/281,037

(22) PCT Filed: Oct. 1, 2019

(86) PCT No.: PCT/EP2019/076642
§ 371 (c)(1),
(2) Date: Mar. 29, 2021

(87) PCT Pub. No.: WO2020/070158
PCT Pub. Date: Apr. 9, 2020

(65) Prior Publication Data
US 2021/0345748 A1    Nov. 11, 2021

(30) Foreign Application Priority Data

Oct. 2, 2018  (FR) ........................................ 1859122

(51) Int. Cl.
*A45D 7/04* (2006.01)
*A61Q 5/04* (2006.01)

(52) U.S. Cl.
CPC ................. *A45D 7/04* (2013.01); *A61Q 5/04* (2013.01); *A45D 2200/057* (2013.01); *A61K 2800/87* (2013.01)

(58) Field of Classification Search
CPC .... A45D 19/00; A45D 19/0083; A45D 19/02; A45D 19/16; A45D 19/0041;
(Continued)

(56) References Cited

U.S. PATENT DOCUMENTS

| | | |
|---|---|---|
| 1,693,248 A | 11/1928 | Newton |
| 2,033,812 A | 3/1936 | Brewer |

(Continued)

FOREIGN PATENT DOCUMENTS

| | | |
|---|---|---|
| EP | 0131838 A2 | 1/1985 |
| EP | 1954893 A2 | 8/2008 |

(Continued)

OTHER PUBLICATIONS

Japanese Patent Office issued for Japanese Pat. App. No. 2021-518123 mailed Jun. 6, 2022 (7 pages).
(Continued)

*Primary Examiner* — Rachel R Steitz
(74) *Attorney, Agent, or Firm* — Shumaker, Loop & Kendrick, LLP (57) ABSTRACT

A hair treatment method, including the step of spraying onto the hair a composition for changing the form of the hair, notably a permanent-waving or curl-reducing composition, using a device, called a low flowrate device, comprising at least two nozzles oriented such that their respective jets collide, these nozzles being supplied with said composition at pressure, the total flowrate of composition delivered by the nozzles being between 0.1 and 3 L/min, preferably between 0.2 and 2 L/min, and even more preferably between 0.3 and 1 L/min.

18 Claims, 1 Drawing Sheet

(58) Field of Classification Search
CPC .... A45D 2019/0033; A45D 7/00; A45D 7/02; A45D 7/04; A45D 7/045; A45D 7/06; A45D 7/065; A45D 2200/056; A61Q 5/04; A61K 2800/87

See application file for complete search history.

(56) References Cited

U.S. PATENT DOCUMENTS

| | | | |
|---|---|---|---|
| 2,076,688 | A | 4/1937 | West |
| 2,807,269 | A | 9/1957 | Lembo |
| 4,376,441 | A | 3/1983 | Duncan |
| 4,792,250 | A | 12/1988 | Turner |
| 5,551,453 | A * | 9/1996 | Sturla .................. A61Q 5/04 132/202 |
| 6,205,597 | B1 | 3/2001 | Shimizu |
| 6,402,776 | B1 | 6/2002 | Martin |
| 6,955,176 | B2 | 10/2005 | Ackermans et al. |
| 2005/0087631 | A1 | 4/2005 | Ursic |
| 2011/0120487 | A1 | 5/2011 | Rollat-Corvol et al. |
| 2015/0128983 | A1 * | 5/2015 | Vic ...................... A45D 6/00 132/204 |
| 2016/0051025 | A1 | 2/2016 | Rollat-Corvol et al. |
| 2020/0038891 | A1 | 2/2020 | Tojo et al. |
| 2020/0315319 | A1 | 10/2020 | Samain |
| 2021/0153619 | A1 | 5/2021 | Robinault et al. |

FOREIGN PATENT DOCUMENTS

| | | |
|---|---|---|
| ES | 2393548 T3 | 12/2012 |
| FR | 2931644 A1 | 12/2009 |
| FR | 2931665 A1 | 12/2009 |
| FR | 3061498 A1 | 7/2018 |
| JP | S-6036009 A | 2/1985 |
| JP | H0291654 U | 7/1990 |
| JP | H07-275751 A | 10/1995 |
| JP | 3097586 U | 1/2004 |
| JP | 2006-158529 A | 6/2006 |
| JP | 2015-113287 A | 6/2015 |
| JP | 5955297 B2 | 7/2016 |
| KR | 20160102597 A | 8/2016 |
| TW | I-616159 B | 3/2018 |
| WO | 0027240 A1 | 5/2000 |
| WO | 2004101163 A1 | 11/2004 |
| WO | 2009145400 A1 | 12/2009 |
| WO | 2014154889 A1 | 10/2014 |

OTHER PUBLICATIONS

International Search Report for PCT/EP2019/076642 mailed Nov. 11, 2019 (3 pages).
Written Opinion for PCT/EP2019/076642 mailed Nov. 11, 2019 (6 pages).
International Search Report for PCT/EP2019/076624 mailed Nov. 6, 2019 (3 pages).
Written Opinion for PCT/EP/2019/076624 mailed Nov. 6, 2019 (5 pages).
International Search Report for PCT/EP2019/076639 mailed Nov. 11, 2019 (4 pages).
Written Opinion for PCT/EP2019/076639 mailed Nov. 11, 2019 (6 pages).
International Search Report for PCT/EP2019/076634 mailed Nov. 6, 2019 (3 pages).
Written Opinion for PCT/EP2019/076634 mailed Nov. 6, 2019 (5 pages).
Japanese Patent Office issued for Japanese Pat. App. No. 2021-518130 mailed Mar. 8, 2022 (6 pages).
Indian First Examination Report issued for Indian Pat. App. No. 202117013569 mailed May 26, 2021 (5 pages.).
Indian First Examination Report issued for Indian Pat. App. No. 202117014594 mailed Jul. 30, 2021 (5 pages).
Non-Final Office Action (NFOA) issued for U.S. Appl. No. 17/281,061, mailed Jun. 7, 2023 (12 pages).
Final Rejection (FR) for U.S. Appl. No. 17/281,061, mailed Dec. 7, 2023 (14 pages).
Unity of Invention Requirement issued for U.S. Appl. No. 17/281,074, mailed Feb. 26, 2024 (7 pages).
Non-Final Office Action (NFOA) issued for U.S. Appl. No. 17/281,074, mailed Jul. 1, 2024 (13 pages).
Unity of Invention Requirement issued for U.S. Appl. No. 17/281,047, mailed Sep. 4, 2024 (8 pages).
Notice of Allowance issued for U.S. Appl. No. 17/281,061 mailed Apr. 10, 2024 (11 pages).

\* cited by examiner

HAIR TREATMENT METHOD

TECHNICAL FIELD AND BACKGROUND

The present invention relates to a hair treatment method.

Within the field of changing the form of hair, with a view to achieving curls, or reducing or straightening curls, there is a need to apply compositions and to place them in contact with the hair. Such compositions are based on active substances, such as sulfur-containing reducing agents or alkaline agents with a very alkaline pH. They either have an unpleasant odor or irritate the skin, which has led the profession to favor application methods that minimize contact.

In the case of permanent waving (for curling the hair), use is made of compositions based on sulfur-containing ingredients, such as thiols or sulfites. In the past, the practice was to apply the product to the hair before rolling the latter onto rollers. Nowadays, it is recommended to roll the hair onto rollers and then to apply the product to the hair once rolling is complete, thereby limiting contact with the hands. The problem that has been identified is that the product slowly diffuses between the hairs, and the lengths that are closer to the roller receive less product than do the roots, which are near the periphery. To solve the problem, use has been made of special formulations having a higher concentration of active substances. The ends of the hair are thus treated to a greater degree, but the roots receive more active substance to no useful purpose, which gives rise to problems of overdosing and sometimes problems of hair breakage, particularly if a bend forms in the hair when the roller is put in place. This problem occurs very infrequently, of course, but as it can be very detrimental to the client it is a factor in a move away from permanent waving. To counter this, the hair stylist has the option of employing a traditional application method, but prefers not to do so since he/she wishes to avoid contact between the product and his/her hands. He/she may also apply the product to the hair before rolling and then roll the hair while wearing leaktight gloves. The rolling process may, however, be long and tedious.

Two techniques are used in the case of treatments for reducing curls (curl relaxing or straightening), based respectively on thiol-based compositions or on high-pH alkaline-based compositions. It is difficult to apply the product evenly because, in this case, too, there is a desire not to touch the product. In point of fact, application of the product requires that locks of hair be treated individually, and thus that they be moved one relative to another. In these instances, thickened products are therefore used, these helping to avoid the hairs becoming tangled together. The problem is that these products form a layer around the hairs, which can give rise to issues of overdosing.

EP0131838 discloses an applicator for a targeted application of a hair treatment composition.

JP H0291654 discloses a shower head.

In either situation, there is an unresolved need to apply form changing products in such a way as to achieve an even application but without having to touch the hair.

SUMMARY

The invention aims to meet this need and achieves that end by virtue of a hair treatment method, comprising the step consisting in spraying onto the hair a hair form changing composition, in particular a permanent-waving or curl-reducing composition, using a distribution device, called a low flowrate distribution device, comprising at least two nozzles oriented such that their respective jets collide, these nozzles being supplied with said composition under pressure, the total flowrate of composition delivered by the nozzles being between 0.1 and 3 L/min, preferably between 0.2 and 2 L/min, and even more preferably between 0.3 and 1 L/min.

The use of such a device, also called a low-flowrate shower device, with form changing treatments makes it possible to achieve an even result while not requiring the hair or the product to be touched.

The fact that the flowrate is relatively low avoids a loss of composition into the sink plughole; furthermore, the hair is not made so wet that it becomes excessively weighed down, thereby preventing access within the mass of the hair, which would require the hair stylist to lift up the hair manually and expose himself/herself to the product, this being precisely that which it is desired to avoid.

The composition may be obtained by mixing, into water, a hair form changing product comprising one or more active substances influencing the form of the hair once the latter is dry. These active substances are permanent-waving or curl-reducing or straightening active substances. The form changing composition may comprise active substances chosen notably from thioglycolic acid or salts thereof (ammonium thioglycolate, also referred to as TGA), derivatives of thiolactic acid or the salts thereof (ammonium thiolactate, also referred to as TLA), cysteine or the salts thereof and derivatives thereof, cysteamine, the salts and derivatives thereof, sulfites, bisulfites, and strong bases such as sodium hydroxide, guanidine compounds and salts thereof, lithium hydroxide, potassium hydroxide and mixtures thereof.

Permanent-Waving Treatment

In the present case the hair form changing composition is a permanent waving composition. The invention thus allows the ends of the hair to be properly treated.

In the case of permanent waving the method comprises a step of rolling the hair around at least one roller prior to application of the composition using the device. This application is followed by an exposure time. One advantage of the invention is that it is possible to reduce this exposure time to 15 minutes or less, 20 minutes customarily being necessary in the traditional method.

The head of the device bearing the nozzles is preferably placed at a distance of at least 10 cm from the roller, the composition being sprayed onto the hair rolled around this roller.

The composition is preferably formed by injecting a permanent-waving product, such as a thiol- or bisulfate-based product, into a flow of water, in a ratio such that the composition contains from 1 to 20% by weight of form changing active substance(s) to the total weight of the composition.

The application time is, for example, between 5 and 15 s, notably of the order of 10 s, for a standard head of hair and a flowrate of 1 L/min.

The application of the composition may be followed by rinsing, or by a phase of neutralizing with an oxidant then rinsing, and then unwinding of the lock of hair rolled on the roller.

Preferably, for treating long hair, the method comprises the following steps:
1) placing rollers in the hair,
2) applying water to the hair rolled around the rollers using the low-flowrate distribution device according to the invention; in this step, the water conveyed onto the hair may not contain any hair form changing active substance;

3) applying the form changing composition using the low-flowrate device according to the invention.

Preferably, the head of the device is placed at a distance of at least 10 cm from the rollers.

In a particular embodiment of the invention, the concentration of permanent-waving product and/or the flowrate of permanent-waving composition delivered onto the hair is varied in step with the movement of the device relative to the hair. This variation may be controlled by the user by virtue of a control member present, for example, on the handpiece bearing the nozzles. In a variant, this variation is controlled by an electronic circuit that detects, for example optically detects, a relative movement of the handpiece with respect to the hair and modifies the flowrate and/or the concentration as a function of this movement and as a function of a predefined rule pertaining to the evolution of the flowrate and/or of the concentration.

This approach is especially advantageous:
when the hairstyle involves differences in curl tightness, as is often the case in sunny climes, with loose curls on the outer parts of the hair and tight curls in the inner parts of the hair;
when the hairstyle involves differences in hair condition, as is the case of highlighted hair.

The permanent-waving composition may be formed by injecting a permanent-waving product into a flow of water such that the concentration of permanent-waving product injected into the flow of water is between 1 and 100% and preferably between 10 and 40% by weight relative to the total weight of the composition delivered onto the hair.

The permanent-waving composition may comprise one or more active substances chosen from thioglycolic acid or the salts thereof (ammonium thioglycolate, also referred to as TGA), derivatives of thiolactic acid or the salts thereof (ammonium thiolactate, also referred to as TLA), cysteine or the salts thereof and the derivatives thereof, cysteamine, the salts and derivatives thereof, sulfites, bisulfites and mixtures thereof.

The total concentration of this or these active substance(s) in the composition delivered onto the hair by the device is preferably between 1 and 20% by weight relative to the total weight of the composition.

The total concentration of this or these active substance(s) in the product injected into the flow of water is preferably between 0.1 and 40%, more preferably between 0.1 and 12% by weight relative to the total weight of the product.

In a particular case, the total concentration of active substance in the product may be as much as 100% in the case of solid compounds such as cysteine.

Curl-Reduction Treatment

In the present case the hair form changing composition is a curl-relaxing or straightening composition.

"Curl relaxing" should be understood to mean that the composition tends to increase the radius of curvature and/or decrease the number of the curls.

The curl-relaxing or straightening composition may be formed by injecting a curl-relaxing or straightening product into a flow of water such that the concentration of curl-relaxing or straightening product injected into the flow of water is between 1 and 100% by weight and preferably between 10 and 40% by weight relative to the total weight of the composition delivered onto the hair.

The curl-relaxing or straightening composition may comprise one or more active ingredients chosen from thioglycolic acid or salts thereof (ammonium thioglycolate, also referred to as TGA), derivatives of thiolactic acid or the salts thereof (ammonium thiolactate, also referred to as TLA), and strong bases such as sodium hydroxide, guanidine compounds and salts thereof, lithium hydroxide, potassium hydroxide and mixtures thereof.

The total concentration of these active substances in the composition delivered onto the hair by the device is preferably between 0.2 and 20% by weight relative to the total weight of the composition.

The total concentration of this or these active substance(s) in the product injected into the flow of water is preferably between 0.1 and 40% by weight, preferably between 1 and 12% by weight relative to the total weight of the product.

In a particular case, the total concentration of active substance in the product may be as much as 100% in the case of solid compounds such as sodium hydroxide, potassium hydroxide and lithium hydroxide.

The method preferably comprises the step consisting in directing the jets emitted by the nozzles toward the roots such as to plaster the hair onto the scalp. Then, once the curls have been flattened, the head of the device is moved toward the ends of the hair.

In a preferred manner, between 5 and 15 seconds, for example approximately 10 seconds, are taken to plaster down the roots and then between 5 and 15 seconds, for example approximately 10 seconds, are taken to move the head of the device and to apply the composition to the lengths.

A method of this type makes it possible to impregnate the hair with composition without soaking it excessively. The hair is thus straightened and it is possible to comb or to brush it without curls re-forming. Straightened hair placed in this aligned fashion may be left for an exposure time of preferably 10 to 60 minutes before the treatment is completed.

As in the case of permanent waving, there is no useful purpose in touching the hair or the product-impregnated hair.

It is possible to rinse with a conventional flow of water or with the low-flowrate device according to the invention, preferably at a flowrate of 1 to 3 L/min. Rinsing requires a very limited quantity of water—approximately 2 L for the entire head of hair instead of the 10 L or more in the conventional method using thickened product.

A further advantage of the invention is that it is possible to pass a heated hair iron through the hair, at approximately 200° C. for example, before or after rinsing, without drying the hair beforehand and without producing a great deal of steam. This allows a time-saving as compared to the conventional method, which requires the hair to be dried before the heated hair styler is passed through it.

In a particular embodiment of the invention, the concentration and/or the flowrate of the hair form changing composition is varied in step with the movement of the device relative to the hair. This approach is especially advantageous when the hairstylist is treating regrowth, since the roots require more active substance than do the lengths.

Advantageously, the flow of liquid conveyed to the head of the device comprises a foaming agent, such as a surfactant. By virtue of the speed of the flow arriving on the hair, it will, by foaming, give rise to three advantageous effects:
the foam makes it possible to see the areas that have been treated, and to identify those that have not been treated and those that have been insufficiently treated (and that need the application to be continued);
the hair is subject to a wetting effect and thus, despite the low level of the flow, the hair is better impregnated;
the hair can be compacted, which is useful in terms of straightening.

It is possible to vary the concentration of active substance(s) by adapting how the product comprising this or these active substance(s) is incorporated into the water flow. The device may be arranged such as to allow adjustment of the quantity of product injected into the water flow per unit of time.

It is also possible to vary the pH thereof, for example by injecting a pH-modifying agent, or to vary the nature of the active substances by employing at least two sources of active substances that may be selected and/or of which the respective influx thereof into the flow may be adjusted.

In one illustrative embodiment, use is made of two supplies for supplying the head of the device, namely a first supply comprising water or a first active substance in water, and a second supply comprising a second active substance in water. In one example, the first supply comprises a thioglycolic acid (TGA) derivative and the second supply comprises cysteine. One at least of the two supplies may comprise a pH-regulating agent: For example, TGA for the first supply and monethanolamine for the second supply, or sodium hydroxide for the first supply and citric acid for the second supply.

The use of two supplies where the ratio of one to the other can be controlled by the user or automatically makes it possible to vary the force of the composition in accordance with the position of the device within the head of hair. It also makes it possible to adapt the treatment to the person being treated, for example using adjustment data stored in a memory or chosen in accordance with the situation thereof or the ultimate aim thereof.

The supplies may be controlled by an expert system such as faithfully to reproduce the ideal formulations for each client or each situation.

Preferably, in the case of a plurality of supplies, the device is arranged such that the products injected into the respective supplies do not mix inside the device.

For example, the device comprises two sets of nozzles, each supply delivering the composition corresponding to a respective set of nozzles, the sets of nozzles being arranged in adjacent one another on the handpiece of the device.

If the device comprises a plurality of supplies, each having a water flow into which a product is injected, and a set of nozzles for delivering the flow thus formed, the water constituting the flow of each supply can originate from a single source, for example mains water, and/or one and the same pump. In a variant, the water flow of each supply is pressurized by a respective pump.

The method may comprise the application of a gelling agent or a thickening agent, delivered onto the hair by, for example, a set of dedicated nozzles that are different from the nozzle delivering the hair form changing composition.

This gelling agent or this thickening agent is preferably chosen from derivatives of sugar such as polysaccharide derivatives, such as guar, carraghenan and cellulose gums.

The device according to the invention may thus also comprise a foodstuff as gelling agent or thickening composition, contained in a specific reservoir.

In one illustrative embodiment of the invention, the method comprises:
1) the application of the hair form changing composition to the hair and then the application of a thickened composition; or
2) the application of the hair form changing composition simultaneously with application of a thickened composition. In this latter case, the device is preferably oriented such that the flow of the hair form changing composition precedes that of the thickened composition, and such that preferably the flows do not mix at the moment when they are emitted by the device. "Precedes" should be understood to mean that, the device being moved in one direction relative to the hair, a given area of the head of hair thus first receives, as a result of this movement, the flow of form changing composition before receiving the thickened composition on top of that. "Thickened composition" should be understood to mean a composition containing at least one gelling agent or one thickening agent, preferably in a sufficient amount for the viscosity of the thickened composition to be higher than that of the form changing composition; it is possible for the thickened composition not to contain any form changing active substance.

This second variant is especially advantageous for hair stylists who have a particular liking for the thickened and even creamy appearance of curl relaxing products. With this particular embodiment, they will have this creamy appearance without risking the overdosing inherent in the thickened appearance. Another advantage is that the hair stylist will not smell the odors.

To facilitate the hair stylist's work, provision may be made for another low-flowrate distribution device according to the invention for rinsing and/or conveying hydrogen peroxide. The user then has two handpieces, one for the distribution of at least a first active substance and another for the distribution of water and/or at least one other active substance that is different from the first active substance. These two handpieces may be connected to one and the same base station that, for example, controls the pressure of the flow delivered by the nozzles of each handpiece and/or controls the concentration of active substance in the flow. The two handpieces may, furthermore, be connected to two respective base stations. It is possible, also, to integrate two different sets of nozzles into one and the same handpiece, for delivering two different compositions.

The device may be configured to function with a product in pulverulent or concentrated form and comprise a reservoir for receiving this product. For example, the reservoir comprises a cover that may be opened for the introduction therein of a quantity of powder intended for one use and then closed again. The reservoir is arranged such that water comes into contact with the product contained in the reservoir. When the product is a powder, the water passing into the reservoir dissolves the powder and the latter is thus incorporated into the flow. This possibility is especially advantageous in the case of active substances such as sodium hydroxide or cysteine, which can easily be in the form of a powder.

The method may comprise the application of a care composition to the hair, for example a silicone, an oil or a cationic compound.

The method may comprise the application of an inhibitor composition to the hair, for example in a localized fashion to a given area in order to protect against a risk of overdosing of the hair form changing composition.

The method may comprise the application of an activating composition to the hair, designed to facilitate or to boost the action of the form changing composition, the activating composition comprising, for example, a thiol or an alkaline agent.

The form changing composition may be applied to dry or wet hair.

In an illustrative embodiment, the form changing composition is delivered onto dry hair, which enhances absorption and thus penetration. Preferably, the injection rate ranges from 1% to 100% and more preferably from 2% to 40%. This rate is preferably constant. For example, approximately 10 to 20 seconds are required for treating the hair.

After application of the form changing composition to the hair, it is possible to stop the device and to wait at least 10 seconds, preferably several tens of seconds. The surplus is eliminated naturally under gravity within less than a minute. Optionally, it is possible to wipe off areas that should not have been covered.

The handpiece may comprise a screen to avoid splashing. This screen is preferably arranged such as to be secured removably on the body of the handpiece.

The method may comprise the application of heat or of a flow of hot or cold air to the hair, for example in order to accelerate drying.

The device may thus comprise an outlet for hot or cold air, incorporated, for example, in the handpiece, for directing the hot or cold air onto the hair.

The device may also comprise a heating surface, for example a heating plate, with which the hair is brought into contact; this heating surface may be integrated into the handpiece if appropriate.

The form changing composition may be delivered onto the hair at a temperature higher than or equal to 25° C., notably in order to enhance comfort and to induce activation. The device may thus be arranged such as to heat up the water flow conveyed into the nozzles and/or supplied from mains hot water. If the device comprises a heating-up device for heating up the water and uses a pump for raising the pressure of the flow conveyed to the nozzles, the heating-up device is then preferably placed downstream of the pump.

Low-Flowrate Distribution Device

Another subject of the invention is the device for implementing the method according to the invention, as defined above.

The device according to the invention, used to distribute the form changing composition, comprises a handpiece, also called a low-flowrate shower device, which bears the nozzles.

The jets are emitted at a relatively high speed, preferably in excess of or equal to 8 m/s or, better still, 15 m/s, which gives rise to a fragmentation of the jets when they meet. The speed at the outlet from the nozzles is, for example, over 5 m/s, notably 8 m/s approximately.

The nozzles are borne by one or more heads of the device.

The pressure upstream of the nozzles may be obtained from the mains water supply, when that is sufficient, or by means of a pump. The low-flowrate device according to the invention may thus advantageously comprise a pump, for example a centrifugal pump, connected to the nozzles. This pump can be supplied with hot or cold running water, or by a reservoir containing water and including additives, if appropriate.

The axes of the nozzles preferably form an angle with one another of between 30° and 120°. This makes it possible to convert their kinetic energy into a reduction in droplet size and as a result to achieve a flow that wets while using a reduced quantity of water. The nozzles are, for example, circular orifices of between 0.1 and 2 mm in diameter.

The supply pressure to the nozzles may be in excess of or equal to 2 bar, notably between 2 and 25 bar and, better still, between 4 and 20 bar.

The surface area impacted by the flow emitted by the device may be between 10 and 1000 cm², preferably from 50 to 3000 cm². To measure this surface area, the handpiece bearing the nozzles is kept stationary relative to the impacted surface area and the area covered is calculated manually after 1 second of application. When the device is used, the distance separating the nozzles from the area at which the flow is directed is preferably between 1 and 30 cm. The device may comprise a handpiece comprising two sets of nozzles connected to two respective supplies, each set of nozzles comprising two nozzles of which the jets meet. These two sets of nozzles may be arranged side-by-side on the handpiece. One of the supplies may contain at least one permanent-waving or curl-reducing cosmetic active substance; the other supply may contain a gelling agent or a thickening agent.

BRIEF DESCRIPTION OF THE DRAWINGS

The invention may be better understood from reading the following detailed description of non-limiting illustrative embodiments thereof and from examining the appended drawing, in which.

DETAILED DESCRIPTION

Figure 1:
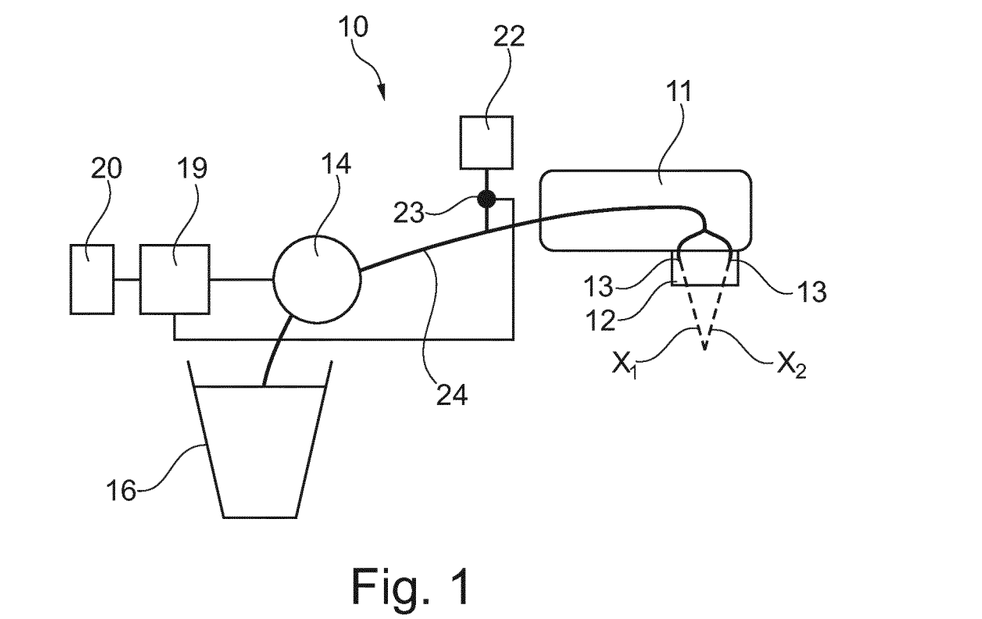
FIG. 1 is a partial schematic representation of an example of a device according to the invention.

FIG. 1 shows a low-flowrate distribution device 10 according to the invention, comprising a handpiece 11, also called a "low-flowrate shower device", for delivering the form changing composition onto the hair, as detailed above.

The handpiece 11 preferably comprises, as illustrated, a distribution head 12 having at least two nozzles 13 each delivering a respective jet under pressure.

The $X_1$ and $X_2$ axes of the nozzles 13 are oriented such that their jets collide, thereby making it possible to reduce the size of the droplets. The nozzles 13 allow the drops to reach a small size and a speed preferably in excess of 8 m/s after the jets have collided.

Such an arrangement of nozzles is described in the Creaholic S.A. patent EP 1 954 893 B1 and can be reproduced. The angle between the $X_1$ and $X_2$ axes is, for example, of the order of 90°.

Figures 2, 3:
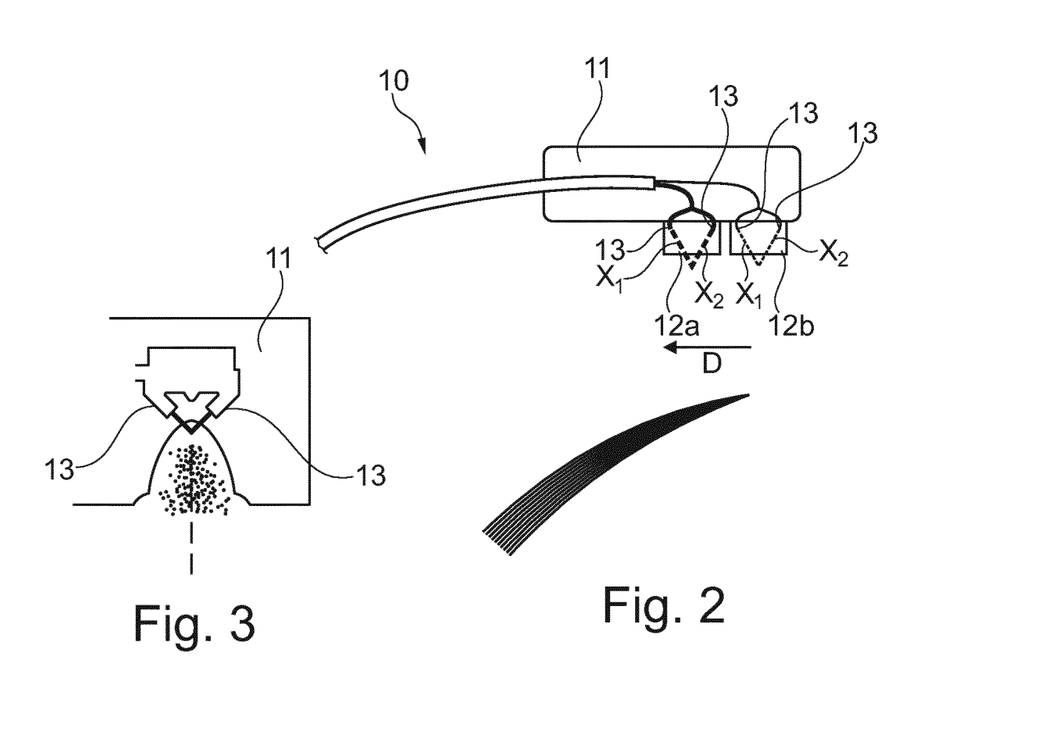
FIG. 2 is a view, similar to FIG. 1, of a variant embodiment of the invention.
FIG. 3 shows an example of an arrangement of the nozzles within the handpiece.

The handpiece 11 may have a cavity 89 that is open toward the outside, within which the jets emitted by the nozzles 13 meet, as illustrated in FIG. 3. This cavity may diverge outward, with a recess further widening it close to its opening. The cavity may play a part in guiding the flow generated after the jets meet in the axis of said cavity, toward the outside.

The speed of the droplets measured at the opening of the cavity, in the axis thereof, may be in excess of or equal to 8 m/s.

In this example, the device 10 operates with a supply from a reservoir 16, for example a tub filled with the solution to be distributed. In a variant, the device is supplied by hot or cold mains water.

The device 10 may comprise a pump 14 for raising the pressure upstream of the nozzles 13 to a value in excess of or equal to 4 bar. The pump 14 is, for example, a centrifugal pump. In a variant, the composition is pressurized by other means, such as, for example, the use of a sufficient drop in level between the reservoir 16 and the handpiece 11.

An electronic control system 19, for example comprising a microcontroller, may be provided for controlling the operation of the various constituent elements of the device 10, notably obtaining the desired flowrate at the outlet, if appropriate.

The control system 19 may comprise, if appropriate, a man-machine interface 20 that makes it possible to adjust various operating parameters.

According to the invention, the flowrate of fluid delivered by the handpiece 11 is between 0.1 and 3 L/min.

The hair form changing composition is formed by injecting a form changing product, contained in a reservoir 22 in liquid form, for example, into the water flow upstream of the nozzles 13.

A flowrate adjustment member 23, such as a solenoid valve or a pump, may be present for controlling the quantity of product injected into the water flow from the reservoir 24. This member 23 is controlled by the control circuit 19.

In the variant illustrated in FIG. 2, the device 10 comprises two sets of nozzles 13 borne by the respective heads 12a and 12b of the handpiece 11.

Two supply circuits supply the heads 12a and 12b, for example with a thickened composition and a form changing composition, respectively.

In the present case, the handpiece 11 is moved in a direction D relative to the hair, such as successively to deposit the thickened composition and the form changing composition onto one and the same area of the hair. The sets of nozzles 13 delivering the thickened composition and the form changing composition may follow one another along the longitudinal axis of the handpiece, as illustrated.

EXAMPLES

Example 1

A device according to the invention, as illustrated in FIG. 1, was used with a total flowrate of composition delivered by the nozzles of 2 L/min. The diameter of the nozzles was 0.6 mm, the angle between the nozzles was 90°, and the supply pressure to the nozzles was 10 bar.

A form changing product was made with 13% by weight of TGA (ammonium thioglycolate), aqueous ammonia qs pH 9, and water (formula A).

The device was set for 80% by weight injection of formula A into water. In other words, Mc/(Mc+Me)=0.8, where Mc is the weight of formula A injected into the flow per unit of time and Me is the quantity of water constituting the flow prior to mixing with the formula.

In performing the test, the device was used with a supply of hot water (40° C.) and a head of straight hair (Japanese type) of 30 cm.

The hair was rolled onto 13-mm-diameter rollers and then the form changing composition was applied to the rollers 20 cm from the hair by sweeping the area with the flow delivered by the handpiece for 15 seconds.

In parallel, a traditional application was carried out by rolling the hair onto the rollers and then applying formula A with a sponge.

In the first case (invention), all contact with the hands was avoided. In the second case (control), there was a degree of contact between the formula and the fingertips.

Example 1a

On a first head, the exposure time on both sides was 10 minutes, then rinsing was performed and an 8 volume hydrogen peroxide composition at pH 3.2 was applied for 5 minutes. Next a final rinse was carried out and the hair was unrolled.

In the case of the invention, the ends of the hair were found to be very curled (mean diameter of curvature of 30 mm), whereas in the case of the control the ends of the hair were little curled (mean diameter of curvature of 44 mm). In both cases, the roots were the same.

Example 1b

On a second head, the control was repeated with a longer exposure time of 20 minutes, then rinsing was performed and an 8 volume hydrogen peroxide composition at pH 3.2 was applied for 5 minutes. A final rinse was carried out and the hair was unrolled. In the case of the control, the ends of the hair were found to be very curled (diameter of curvature of 30 mm), but the roots were damaged.

Example 2

Formula B was made with 13% by weight of TGA, aqueous ammonia qs pH 9, 8% by weight of LES (sodium lauryl ether sulfate) and water.

Example 2a

A head of 30-cm type-4 curly hair was treated using the device according to the invention. After application for 10 seconds, a brush was passed through the hair. Once brushed out, the hair remained in this position. After 50 minutes rinsing was carried out and the hair treated with straighteners. Rinsing was rapid (1 L of water) and the curls were reduced.

In parallel, the same hair was treated with the same formula manually. A brush was passed through the hair, resulting in tangling that made treatment difficult without placing the hands among the hair. Rinsing was carried out after 50 minutes and the hair treated with straighteners. Rinsing was fairly rapid (1.4 L of water), but the reduction in curls was not uniform.

In parallel, the same hair was treated with a commercial formula, called "X-Tenso Smoothing Cream". Application was performed manually and there was a degree of contact with the hands. A brush was passed through the hair. This operation did not give rise to tangling. Rinsing was carried out after 50 minutes and the hair treated with straighteners. Rinsing was lengthy (9 L of water), and the reduction in curls was not uniform.

Example 2b

The same tests as in Example 2a were performed, with the difference being that the head of 30-cm type-4 curly hair was partially bleached (highlight effect) using Platifiz.

In the first case (invention), there was no overdosing found on the bleached hair. However, in the other two cases (control), the bleached hair was found to be damaged and rough to the touch.

Example 3

Formula C was made, based on citric acid (4%) and monoethanolamine (qs pH 4.5) in water.

Example 3a

The device used was that illustrated in FIG. 2, with two outlets, namely one for formula A and the other for formula C.

The invention enabled the hair stylist to apply formula A and to activate the supply of formula C to the areas he considered to be fragile.

Example 3b

The device of Example 1 was used again, with the difference being that there were two controlled injections into the water flow upstream of the nozzles, one for formula A and one for formula C. The invention enabled the hair stylist to apply formula A and to activate the supply of formula C to the areas he considered to be fragile.

Example 4

The following formula D was prepared:

| | |
|---|---|
| Propylene glycol | 2 g |
| White mineral oil | 8 g |
| (Klearol, from Sonnebom) | |
| Vaseline | 10 g |
| Non-ionic surfactant | 4 g |
| MIXTURE OF CETYLSTEARYL ALCOHOL, OXYETHYLENE SORBITAN MONOSTEARATE (20 EO) (80/20) | |
| Water qs | 100 g |

The same device as in Example 3a was used again. The hair stylist carried out application from the root to the ends of the hair. Formula A was applied and then formula D was applied on top. The hair stylist found there to be a straightening cream appearance, but without the drawbacks of the latter. The odor of formula A was absent.

In these examples it will be noted that the invention makes it possible to apply the hair form changing formula more effectively and without having to come into contact with it. A change in form that was of better quality (more uniform) or more precisely targeted (roots) was achieved. The product penetrated deeply, as far as the roots, and made it possible to obtain an effect without overdosing.

The invention is not limited to that which has just been described. A plurality of products may notably be conveyed in the flow supplying the nozzles with a view to achieving, for example, a personalization effect.

The invention claimed is:

1. A hair treatment method, comprising the step of spraying onto hair a hair form changing composition, using a device, called a low flowrate device, comprising at least two nozzles oriented such that their respective jets collide, these nozzles being supplied with said composition under pressure, the total flowrate of composition delivered by the nozzles being between 0.1 and 3 L/min, wherein the hair form changing composition being formed by injecting a form changing product into a water flow upstream of the nozzles.

2. The method as claimed in claim 1, a hair form changing composition being a permanent-waving composition, the method comprising the application of the composition using said device on hair previously rolled onto at least one roller.

3. The method as claimed in claim 2, comprising the following steps:
placing rollers in the hair,
applying water to the hair rolled onto the rollers, using the low-flowrate distribution device,
applying the form changing composition using the low-flowrate device.

4. The method as claimed in claim 2, wherein the concentration of permanent-waving composition and/or the flowrate of composition delivered onto the hair is varied in step with the movement of the device relative to the hair.

5. The method as claimed in claim 1, the hair form changing composition being a composition for relaxing curls or straightening.

6. The method as claimed in claim 5, comprising the step of directing the jets emitted by the nozzles toward roots of the hair to plaster the hair down onto a scalp, and then, once the curls have been flattened, the step consisting in moving a head of the device toward the ends of the hair.

7. The method as claimed in claim 6, wherein between 5 and 15 seconds are taken to plaster down the roots and then between 5 and 15 seconds are taken to move the head of the device and to apply the composition to lengths of the hair.

8. The method as claimed in claim 5, the hair form changing composition being delivered onto dry hair.

9. The method as claimed in claim 1, wherein two supplies are used to supply a head of the device, namely a first supply comprising a first active substance in water and a second supply comprising a second active substance in water.

10. The method as claimed in claim 1, comprising the application of a gelling agent or thickening agent to the hair.

11. The method as claimed in claim 10, comprising:
application of the hair form changing composition to the hair and then the application of a thickened composition; or
application of the hair form changing composition simultaneously with the application of a thickened composition.

12. The method as claimed in claim 11, comprising the application of the hair form changing composition simultaneously with the application of the thickened composition, and wherein the device is oriented such that the flow of the hair form changing composition precedes that of the thickened composition.

13. The method as claimed in claim 1, the form changing composition being delivered onto the hair at a temperature higher than or equal to 25° C.

14. A hair treatment method, comprising the step of spraying onto hair a hair form changing composition, using a device, called a low flowrate device, comprising at least two nozzles orientated such that their respective jets collide, these nozzles being supplied with said composition under pressure, the total flowrate of composition delivered by the nozzles being between 0.1 and 2 L/min, the hair form changing composition being a permanent-waving composition, the method comprising the application of the composition using said device on hair previously rolled onto at least one roller, the composition being formed by injecting a permanent-waving product into a flow of water in a ratio such that the composition contains from 1 to 20% by weight of form changing active substance(s) to the total weight of the composition.

15. A hair treatment method, comprising the step of spraying onto hair a hair form changing composition, using a device, called a low flowrate device, comprising at least two nozzles oriented such that their respective jets collide, these nozzles being supplied with said composition under pressure, the hair form changing composition being a composition for relaxing curls or straightening, wherein a heated hair iron, is passed over the hair before or after rinsing, without drying the hair beforehand.

16. The method as claimed in claim 15, wherein the concentration and/or the flowrate of the hair form changing composition is varied in step with the movement of the device relative to the hair.

17. The method as claimed in claim 15, the flow of liquid conveyed to a head of the device comprising a foaming agent.

18. The method as claimed in claim 17, wherein the foaming agent is a surfactant.

* * * * *

UNITED STATES PATENT AND TRADEMARK OFFICE
CERTIFICATE OF CORRECTION

PATENT NO. : 12,201,207 B2
APPLICATION NO. : 17/281037
DATED : January 21, 2025
INVENTOR(S) : Henri Samain and Jean-Luc Robinault It is certified that error appears in the above-identified patent and that said Letters Patent is hereby corrected as shown below:

In the Claims

Claim 14, Column 12, Line 50, should read --nozzles being between 0.1 and 3L/min, the hair form--

Signed and Sealed this
Twentieth Day of May, 2025

Coke Morgan Stewart
*Acting Director of the United States Patent and Trademark Office*